United States Patent [19]

Mikhail

[11] Patent Number: 5,405,403
[45] Date of Patent: Apr. 11, 1995

[54] FEMORAL PROSTHESIS WITH ANTI-ROTATION FEATURE FOR BALL

[76] Inventor: W. E. Michael Mikhail, 4203 Shamley Green, Toledo, Ohio 43623

[21] Appl. No.: 210,546

[22] Filed: Mar. 18, 1994

[51] Int. Cl.6 .......................... A61F 2/32; A61F 2/36; A61F 2/40; A61F 2/30
[52] U.S. Cl. ......................................... 623/22; 623/18; 623/19; 623/23; 606/66
[58] Field of Search .................. 623/18, 19, 22, 23; 606/66, 67, 89

[56] References Cited

U.S. PATENT DOCUMENTS

| | | |
|---|---|---|
| 3,102,536 | 9/1963 | Rose et al. |
| 3,658,056 | 4/1972 | Huggler et al. |
| 3,685,058 | 8/1972 | Tronzo |
| 4,005,495 | 2/1977 | Locke et al. |
| 4,012,795 | 3/1977 | Doore et al. ............ 623/23 |
| 4,170,794 | 10/1979 | Zeibig et al. |
| 4,198,711 | 4/1980 | Zeibig |
| 4,224,699 | 9/1980 | Weber |
| 4,225,981 | 10/1980 | Zeibig |
| 4,268,919 | 5/1981 | Zeibig |
| 4,528,702 | 7/1985 | Frey |
| 4,551,863 | 11/1985 | Murray |
| 4,676,797 | 6/1987 | Anapliotis et al. ............ 623/18 |
| 4,687,486 | 8/1987 | Brinckmann et al. |
| 4,705,520 | 11/1987 | Ahrens |
| 4,752,296 | 6/1988 | Buechel et al. ............ 623/23 |
| 4,865,605 | 9/1989 | Dines et al. ............ 623/19 |
| 4,908,034 | 3/1990 | Weightman et al. |
| 4,964,869 | 10/1990 | Auclair et al. ............ 623/23 |
| 5,137,535 | 8/1992 | Keller |

FOREIGN PATENT DOCUMENTS

| | | | |
|---|---|---|---|
| 0124443 | 11/1984 | European Pat. Off. | 623/23 |
| 0393608 | 10/1990 | European Pat. Off. | 623/23 |
| 2619502 | 2/1989 | France | 623/19 |
| 2626169 | 6/1989 | France | 623/23 |
| 2626766 | 8/1989 | France | 623/22 |
| 2631544 | 11/1989 | France | 623/23 |
| 2640497 | 6/1990 | France | 623/22 |
| 2618763 | 11/1976 | Germany | 623/22 |
| 2646842 | 4/1978 | Germany | 623/23 |
| 2724041 | 11/1978 | Germany | 623/18 |
| 3147249 | 6/1983 | Germany | 623/22 |
| 3903438 | 8/1990 | Germany | 623/22 |
| 1130342 | 12/1984 | U.S.S.R. | 623/22 |

OTHER PUBLICATIONS

Osteonics Booklet entitled "Cementless Acetabular Cups-Surgical Protocol", Lit. No. LSP-30 Nov. 1992, Osteonics Corp.
The Journal of Bone and Joint Surgery, vol. 76-B 1994 (Number One Jan.).
Lieberman et al. article entitled "An Analysis of the Head-Neck Taper Interface in Retrieved Hip Prostheses, Clinical Orthopaedics and Related Research", No. 300, pp. 162-167, 1994.

Primary Examiner—David Isabella
Assistant Examiner—Laura Fossum
Attorney, Agent, or Firm—Emch, Schaffer, Schaub & Porcello Co.

[57] ABSTRACT

A hip joint prosthesis includes a stem and integral neck having a tapered wall sized to receive a ball having a cavity for snugly receiving the tapered wall. The neck and the ball have matching configurations with probes and extensions of varying cross-sectional configuration designed to prevent rotation of the ball on the neck.

2 Claims, 3 Drawing Sheets

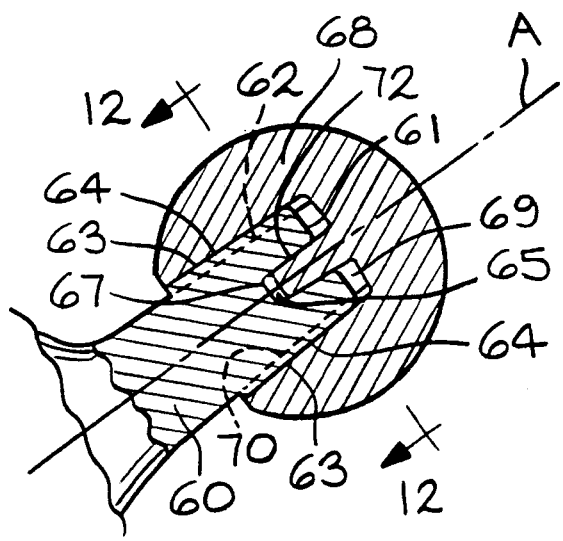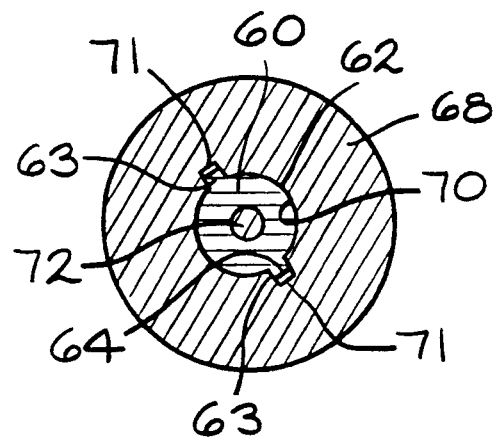
FIG.11  FIG.12
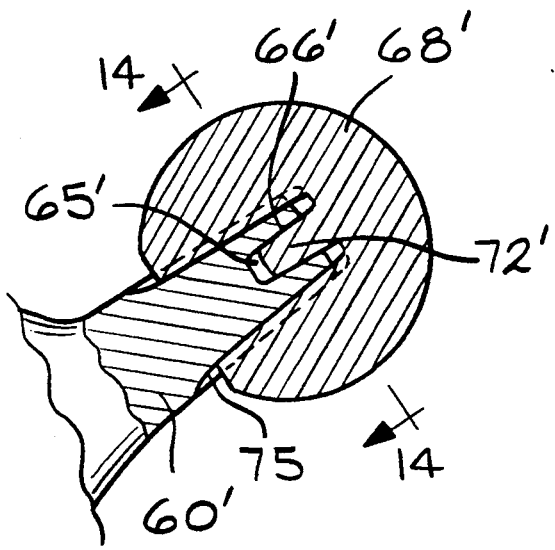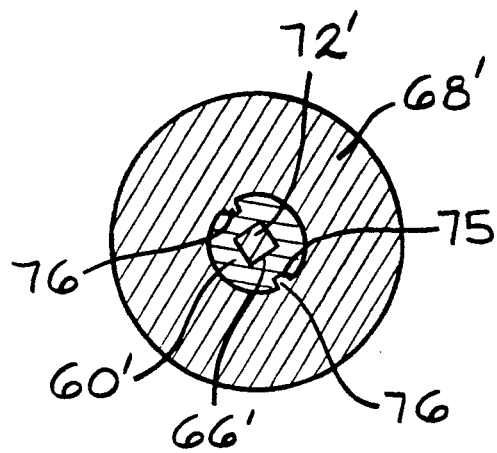
FIG.13  FIG.14

5,405,403

FEMORAL PROSTHESIS WITH ANTI-ROTATION FEATURE FOR BALL

BACKGROUND ART

The present invention relates to a prosthesis for hip joint replacement and includes a femoral component having a stem extending from a proximal end to a distal end intended for implantation in a prepared cavity of the femur, an integral neck extending from such proximal end and a ball or head adapted to be affixed to the neck. As is well known in the art of hip replacement, the ball is intended to be received in an acetabular cup member.

It is important to prevent movement between the ball or femoral head and the neck as any such movement can cause corrosion and wear on the surface of the neck and on the adjoining surface of the ball or head. Any such corrosion can lead to the formation of debris and premature wearing of the prosthesis. A study of such corrosion and wear was reported in an article entitled "Corrosion and Wear At the Modular Interface of Uncemented Femoral Stems" by Stephen D. Cook, Robert L. Barrack and Alistair J. T. Clemow appearing on pages 68–72 of the *Journal of Bone and Joint Surgery*, Vol. 76-B, 1994 No. One (January). Another study was reported in an article entitled "An Analysis of the Head-Neck Taper Interface in Retrieved Hip Prostheses", by Jay R. Lieberman, Clare M. Rimnac, Kevin L. Garvin, Robert W. Klein and Eduardo A. Salvath, appearing on pages 162–167 of *Clinical Orthopaedics and Related Research*, Number 300, March 1994.

DISCLOSURE OF INVENTION

The present invention is directed to a hip joint prosthesis in which the neck and ball or head are configured with mating conical tapers such as a Morse taper for affixing the ball to the neck. When the ball with its internal conical wall is fully seated on the tapered neck, further axial displacement of the ball is prevented by contact of the mating tapered surfaces. In accordance with the present invention, in addition to the mating tapered surfaces, the design incorporates an anti-rotation feature to prevent rotational movement between the ball or head and the conical neck.

BRIEF DESCRIPTION OF THE DRAWINGS

FIG. 11 is a sectional view of a further embodiment of the present invention.

FIG. 12 is a sectional view taken through line 12—12 of FIG. 11.

FIG. 13 is a sectional view of still another embodiment.

FIG. 14 is a sectional view taken through line 14—14 of FIG. 13.

BEST MODE OF CARRYING OUT THE INVENTION

Figure 1:
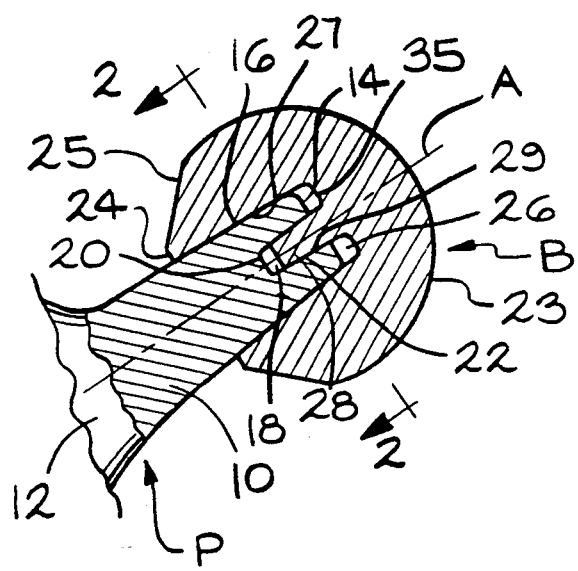
FIG. 1 is a sectional view of a ball or head affixed to the neck portion of a femoral prosthesis manufactured according to one embodiment of the present invention.
Figure 2:
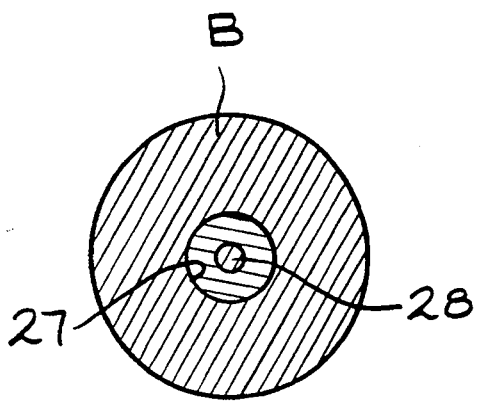
FIG. 2 is a sectional view taken through line 2—2 of FIG. 1.

Referring now to FIGS. 1 and 2, there is provided a fragmentary portion of a femoral stem prosthesis P which includes a stem (not shown) intended for implantation in a prepared cavity of a femur and a neck 10 extending along an axis A from an area 12 adjoining the stem to a free end 14. The stem may be of any desired configuration. The neck 10 has a smoothly polished exterior surface 16 which, in the area adjacent the free end 14, is tapered inwardly toward the axis A as it approaches the free end 14. Preferably, the exterior surface 16 in the area adjacent the free end 14 defines a frustum of a cone, the apex angle of which is in the range of about 2° to 6°.

The neck 10 is provided with a cavity 18 which extends along the axis A from a bottom 20 to the free end 14. The cavity 18 is defined by an interior conical wall 22. The apex angle of the cone defined by the interior wall 22 is between 2° and 6°.

Affixed to the neck 10 is a ball B or head intended for engagement with an acetabular cup (not shown) as is well known in the art. The ball B includes a major portion having a spherical exterior polished surface 23. The ball B of FIG. 1 is provided with a flat end 24 encircling the axis A and a tapered wall 25 joining the spherical exterior surface 23 with the flat end 24.

The ball B is provided with a cavity 26 defined by an interior tapered wall 27 disposed at a matching angle to that of the exterior surface 16 in the area of the neck adjacent the free end 14 so that, when the ball B is affixed to the neck 10, the interior surface 27 of the cavity 26 is snugly engaged to the exterior surface 16 throughout the full distance from the end 24 to the free end 14 of the neck 10. The cavity 26 extends inwardly of the ball B from the flat end 24 to an internal end 35. A tapered probe 28 extends from the internal end 35 into the cavity 26. The tapered probe 28 has an exterior surface 29 defining a conical configuration which matches the configuration of the interior wall 22 by following a similar taper. Thus, when the ball B is engaged to the neck 10 with the interior surface 27 snugly engaged to the exterior surface 16, the exterior surface 29 of the probe will, at the same time, be snugly engaged to the interior wall 22 of the cavity 18. This results in a wedging engagement not only of the neck 10 in the cavity 26 of the ball but also of the probe 28 in the cavity 18 formed adjacent the free end 14 of the neck. Such double tapered engagement provides a firm gripping between the ball B and the neck 10 which prevents rotational movement as well as axial movement of the ball B on the neck 10.

As can be readily seen from FIG. 1, when the ball B is fully seated on the neck 10, the end of the probe 28 is spaced from the bottom 20 of the cavity 18 and the free end 14 of the neck 10 is spaced from the internal end 35 of the cavity 26. Such spacing permits the ball B to be fully engaged to the neck 10 without interference with the result that when fully engaged the adjacent tapered exterior surface 16 and interior surface 27 will be in snug mating engagement and the adjacent interior wall 22 of cavity 18 and the exterior surface 29 of the probe 28 will be in snug mating engagement.

The concept of utilizing a ball having a cavity with an internally tapered wall, known in the art as a Morse taper, on a femoral prosthesis having a neck with a wall having a corresponding taper is well known in the art. See, for example, U.S. Pat. Nos. 4,687,486; 4,012,795; 4,705,520; or 5,171,275, the latter of which I am a co-inventor. However, balls which permit relative micro movement between the interior surface of the ball and the exterior surface of the neck present corrosion and wear problems as set forth in the above referenced articles of Stephen D. Cook et al. and Jay R. Lieberman et al. As is readily apparent, the engagement of the interior surface 27 of the ball with the exterior surface 16 of the neck 10, being disposed at matching tapers, prevents any further axial movement of the ball B toward the prosthesis P when the ball B is fully seated on the neck 10. As previously discussed, balls and prostheses of the prior art utilizing the Morse taper concept are susceptible to some rotational movement of the ball relative to the prosthesis neck as discussed in the above referenced article of Stephen D. Cook et al. and Jay R. Lieberman et al. However, this tendency of the ball to rotate is eliminated by the construction of the neck 10 and ball B as set forth herein.

Figure 3:
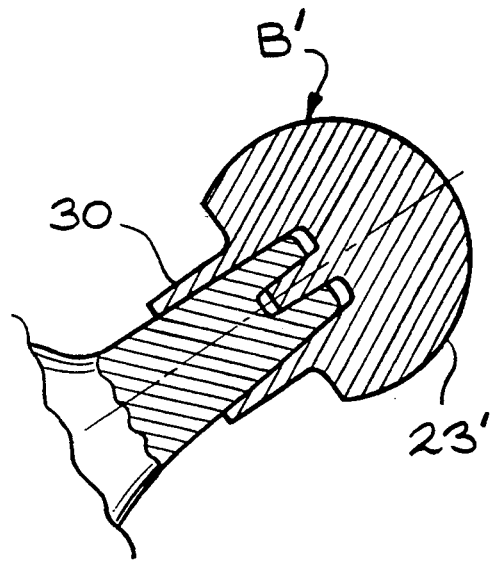
FIGS. 3 and 4 are sectional views showing different types of balls incorporating the anti-rotation feature of the embodiment of FIG. 1.
Figure 4:
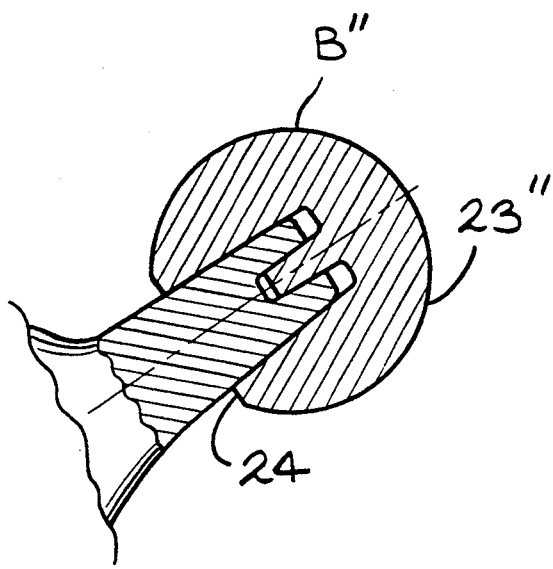

FIGS. 3 and 4 utilize a similar anti-rotation feature but show, in FIG. 3, a ball B' having a skirt 30 which may be utilized where necessary to correct a leg length discrepancy. Similarly, FIG. 4 shows a ball B'' having a spherical exterior surface 23'' which extends completely to the flat end portion 24''. Thus, the anti-rotation feature of the present invention may be used with various types of balls which provide appropriate adjustment for correction of length of leg discrepancy. As is well known in the art, the balls come in a variety of sizes including 22, 26, 28 and 32 mm diameters.

Figure 5:
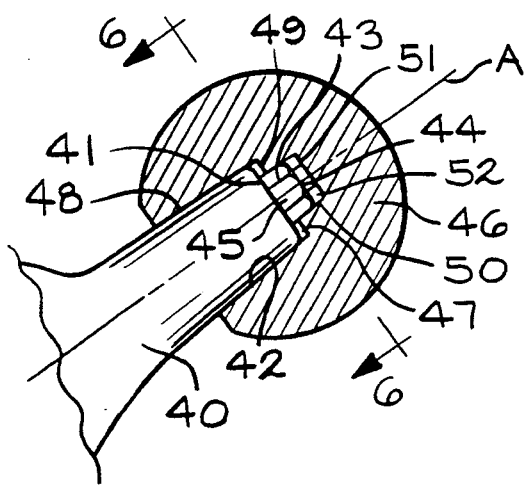
FIG. 5 is a sectional view of a modified embodiment of the present invention.
Figure 6:
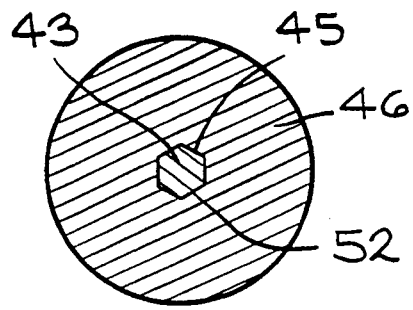
FIG. 6 is a sectional view taken through line 6—6 of FIG. 5.
Figure 7:
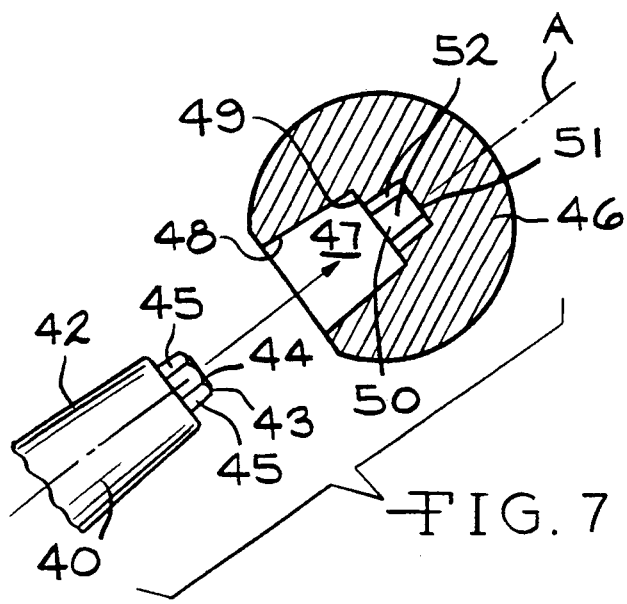
FIG. 7 is an exploded view of the embodiment of FIG. 5.

Referring now to FIGS. 5–7, there is shown a modified embodiment utilizing a different construction for preventing rotational movement between the ball and the neck. Under this embodiment, the femoral stem prosthesis is provided with a neck 40 extending to an end 41 and having a conically tapered exterior surface 42 in the area adjacent the end 41. An integral extension 43 extends from the end 41 to a substantially flat top 44. The extension 43 has a hexagonal cross-sectional configuration and includes a plurality of six flats 45 which are joined together. The flats 45 of the extension 43 may either be disposed at an angle tapering toward the axis A as shown in FIGS. 5 and 7 or, if desired, may be disposed parallel to such axis A.

Affixed to the neck 40 is a ball 46 having a cavity 47 defined by a conical internal wall 48 in an area intended to be contacted by the exterior surface 42 of the neck 40. The cavity 47 extends to an abutment 49 which is positioned to be spaced from the end 41 when the ball 46 is fully engaged to the neck 40. Such positioning permits the conical wall 48 of the ball 46 to snugly engage the exterior surface 42 of the neck when the ball is fully engaged to the neck 40. The ball 46 is also provided with a cavity extension 50 having a hexagonal cross-sectional configuration and defined by an end 51 and a plurality of flats 52 configured and sized to snugly receive the extension 43 when the ball is positioned on the neck 40 such that the flats 52 of the cavity extension 50 are snugly engaged to the flats 45 of the neck extension 43. As can be readily seen, there is a space between the top 44 of the extension 43 and the end 51 of the cavity extension 50. This space permits the ball 46 to be fully seated on the neck 40 without interference in that area. Similarly, the abutment 49 forming the end of cavity 47 is spaced from the end 41 of the neck when the ball 46 is fully seated on the neck 40.

The flats 52 of the cavity extension 50 should be disposed at an angle similar to the angle of the flats 45 of the extension 43 in order that they will snugly engage one another and thus prevent rotation of the ball 46 on the neck 40 while the engaged tapered surfaces prevent axial movement of the fully seated ball 46 on the neck 40.

Figure 8:
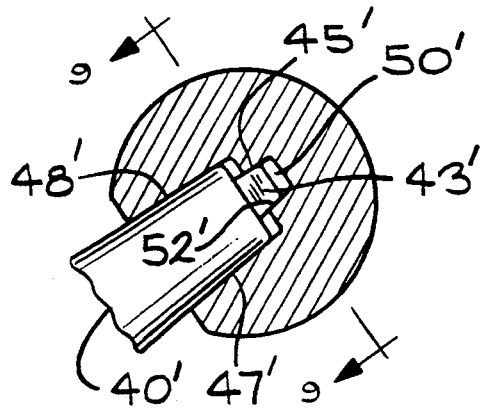
FIG. 8 is a sectional view of yet another embodiment of the present invention.
Figure 9:
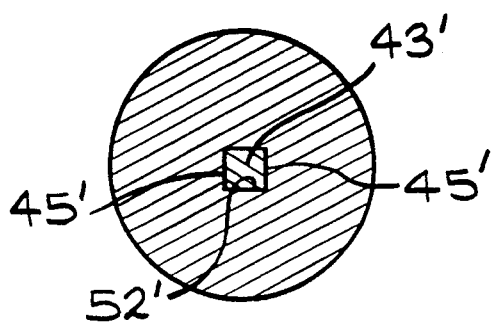
FIG. 9 is a sectional view taken through line 9—9 of FIG. 8.

Referring to FIGS. 8 and 9, there is shown a further embodiment which is similar to the embodiment of FIGS. 5–7 with the exception that the neck 40' has an extension 43' having a square cross-sectional configuration with a plurality of four flats 45' disposed at an angle which is similar to the angle of the conical wall 48' of the cavity 47'. Similarly, the ball 46' has a cavity extension 50' having a square cross-sectional configuration with flats 52' which are disposed at an angle identical to the angle of the flats 45' of the extension 43'.

Figure 10:
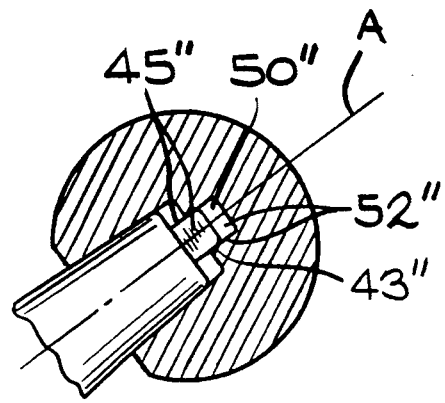
FIG. 10 is a sectional view of an additional embodiment.

FIG. 10 shows a further embodiment in which the extension 43'' has a square cross-sectional configuration; however, the extension 43'' is not tapered and the flats 45'' are parallel to the axis A. Similarly, the cavity extension 50'' has a square cross-sectional configuration sized to snugly receive the extension 43'' and having flats 52'' which are also parallel to the axis A.

Referring now to FIGS. 11 and 12, there is shown yet another embodiment. Under this embodiment there is provided a neck 60 having a tapered portion extending to an end 61. The exterior surface 62 adjacent the end 61 has a generally conical configuration except for a pair of ribs 63 extending outwardly therefrom. Preferably, the ribs 63 are disposed at an angle similar to the angle of the exterior surface 62; however, it is within the contemplation of this invention that the outer edges 64 of the ribs could be parallel to the axis A rather than tapered. The neck 60 is also provided with a cavity 65 extending along axis A inwardly from the end 61. The cavity 65 is similar to the cavity of the embodiments of FIGS. 1 and 2 and has an interior wall tapering inwardly toward the axis A in a direction away from the end 61. The cavity 65 extends to a bottom 67.

The ball 68 has a cavity 69 with an interior wall 70 having a conical configuration of an angle identical to that of the exterior surface 62 of the neck 60. A pair of grooves 71 extend radially outwardly from the interior wall 70. The grooves 71 are sized to snugly receive the ribs 63 of the neck 60. A probe 72 similar to the probe of the embodiment of FIGS. 1 and 2 extends into the cavity 69 and is sized and configured to snugly fit within the cavity 65 when the ball 68 is fully seated on the neck 60.

Referring now to FIGS. 13 and 14, there is provided yet another embodiment. This embodiment is similar to the embodiment of FIGS. 11 and 12 with the exception that the neck 60' is provided with grooves 75 rather than ribs 63 as in the embodiment of FIGS. 11 and 12 and the ball 68' is provided with ribs 76 which are sized and positioned to be snugly received in the grooves 75. Additionally, the cavity 65' and the probe 72' have square cross-sectional configurations.

If desired, in the embodiment of FIGS. 11 and 12 the cavity 65 may be provided with a wall having an interior surface 66 which is cylindrical or other cross-sectional configuration which is parallel to the axis A. In such event, the probe 72 will also have a similar configuration with its wall parallel to the axis A. Similarly, in the embodiment of FIGS. 13 and 14, the cavity 65' may have the interior wall 66 surfaces parallel to the axis A. In such event, the probe 72' will also have a similar configuration with its wall parallel to the axis A.

Many other configurations and modifications will become readily apparent to those skilled in the art. For example, the probe and the cavity in which it is positioned could be triangular or have a clover leaf cross-sectional configuration as well as many other configurations which will effectively prevent rotation of the ball on the neck. Additionally, in lieu of a single probe 28 fitting in a single cavity 18 of the neck 10, a plurality of probes or spikes could extend from the internal end 35 of the ball cavity 26 and engage corresponding recesses formed in the free end 14 of the neck 10. Similarly, probes or spikes could extend from the free end 14 of the neck and be received in corresponding recesses formed in internal end 35 of the ball cavity 26. Accordingly, the scope of the present application should be limited only by the scope of the appended claims.

I claim:

1. A hip joint prosthesis comprising in combination:

(a) a femoral prosthesis having a stem extending from a distal end to a proximal end and a neck having a length extending along an axis from said proximal end to a free end, said neck, in an area adjacent said free end, having (1) an exterior surface tapering inwardly substantially along said lengths toward said axis in a direction toward said free end and (2) at least one rib outwardly from said exterior surface, said rib having an outer edge extending from said free end throughout a major portion of said neck, said outer edge tapering away from said axis in a direction away from said free end; and (b) a ball affixed to said neck free end, said ball having a cavity including (1) an inwardly facing wall and a bottom, at least a major portion of said inwardly facing wall being tapered in a direction and at an angle to provide surface to surface contact between said major portion and said exterior surface and a groove in said cavity having an inwardly facing edge outwardly from said inwardly facing wall extending throughout a length of said inwardly facing wall, said inwardly facing edge tapering at an angle similar to the angle of said rib outer edge.

2. A hip joint prosthesis according to claim 1, wherein said rib outer edge tapers at an angle similar to the angle of said exterior surface.

* * * * *